US010071937B2

(12) United States Patent
Millet et al.

(10) Patent No.: US 10,071,937 B2
(45) Date of Patent: Sep. 11, 2018

(54) METHOD FOR PRODUCING AN OLEFIN BY CATALYTIC CONVERSION OF AT LEAST ONE ALCOHOL

(71) Applicants: ADISSEO FRANCE S.A.S., Antony (FR); CENTRE NATIONAL DE LA RECHERCHE SCIENTIFIQUE, Paris (FR); UNIVERSITE CLAUDE BERNARD, Villeurbanne (FR)

(72) Inventors: Jean-Marc Millet, Lyons (FR); Virginie Belliere-Baca, Vourles (FR); Thi Tuyet Nhung Nguyen, Villeurbanne (FR); Robert Huet, Paris (FR); Patrick Rey, Lyons (FR); Pavel Afanasiev, Decines (FR)

(73) Assignees: ADISSEO FRANCE S.A.S, Antony (FR); CENTRE NATIONAL DE LA RECHERCHE SCIENTIFIQUE, Paris (FR); UNIVERSITE CLAUDE BERNARD, Villeurbanne (FR)

( * ) Notice: Subject to any disclaimer, the term of this patent is extended or adjusted under 35 U.S.C. 154(b) by 197 days.

(21) Appl. No.: 14/765,429

(22) PCT Filed: Feb. 4, 2014

(86) PCT No.: PCT/FR2014/050204
§ 371 (c)(1),
(2) Date: Aug. 3, 2015

(87) PCT Pub. No.: WO2014/118484
PCT Pub. Date: Aug. 7, 2014

(65) Prior Publication Data
US 2015/0361007 A1  Dec. 17, 2015

(30) Foreign Application Priority Data

Feb. 4, 2013 (FR) ..................... 13 50926

(51) Int. Cl.
| | |
|---|---|
| *C07C 1/24* | (2006.01) |
| *C07C 6/04* | (2006.01) |
| *C07C 45/52* | (2006.01) |
| *C07C 45/35* | (2006.01) |
| *C07C 51/25* | (2006.01) |
| *C07C 253/26* | (2006.01) |
| *C07C 319/18* | (2006.01) |
| *C07C 319/20* | (2006.01) |
| *C08F 110/06* | (2006.01) |

(52) U.S. Cl.
CPC ................ *C07C 1/24* (2013.01); *C07C 6/04* (2013.01); *C07C 45/35* (2013.01); *C07C 45/52* (2013.01); *C07C 51/252* (2013.01); *C07C 253/26* (2013.01); *C07C 319/18* (2013.01); *C07C 319/20* (2013.01); *C08F 110/06* (2013.01); *C07C 2527/167* (2013.01); *C07C 2527/18* (2013.01); *Y02P 20/52* (2015.11)

(58) Field of Classification Search
CPC .......... C07C 1/24; C07C 11/06; C07C 45/52; C07C 6/04; C07C 11/04; C07C 11/08; C07C 11/09; C07C 11/167; C07C 47/21; C07C 2527/167; C07C 2527/18; C07C 253/26; C07C 319/18; C07C 319/20; C07C 45/35; C07C 51/252
See application file for complete search history.

(56) References Cited

U.S. PATENT DOCUMENTS 9,056,806 B2 * 6/2015 Adam ....................... C07C 1/20

FOREIGN PATENT DOCUMENTS

| DE | 2048309 A1 | 4/1972 |
|---|---|---|
| GB | 00589709 A | 7/1942 |
| JP | 2008504310 A | 2/2008 |
| JP | 2008531644 A | 8/2008 |
| JP | 2008280349 A | 11/2008 |
| JP | 2009274982 A | 11/2009 |
| JP | 2009544594 A | 12/2009 |
| JP | 2011528687 A | 11/2011 |
| JP | 2012091158 A | 5/2012 |

OTHER PUBLICATIONS

Antonio Morschbacker, "Bio-Ethanol Based Ethylene" Journal of Macromolecular Science, Part C: Polymer Reviews; 2009; vol. 49; pp. 79-84.
Corey B. Philips et al., "Production of Ethylene form Hydrous Ethanol on H-ZSM-5 under Mild Conditions", Ind. Eng. Chem. Res.; 1997; vol. 36; pp. 4466-4475.
Dongsheng Zhang et al., "Effect of P Content on the Catalytic Performance of P-modified HZSM-5 Catalysts in Dehydration of Ethanol to Ethylene" Catal. Lett.; 2008; vol. 124; pp. 384-391.
Eric Linak et al. "CEH Marketing Research Report"; Ethanol; Apr. 2009.
Guillermo A. Saade "CEH Marketing Research Report"; Methanol; Jun. 2009; pp. 1-107.

(Continued)

*Primary Examiner* — Sharon Pregler
(74) *Attorney, Agent, or Firm* — Cantor Colburn LLP

(57) ABSTRACT

The invention relates to a method for preparing an olefine, a diene or a polyene, by catalytic conversion of at least one alcohol having a carbon chain of at least three carbon atoms and different from propan-2-ol, in the presence of at least one catalyst based of at least one phosphate of a metal or several metals M, M being chosen from among the 15 lanthanides (Lanthanum, Cerium, Praseodymium, Neodymium, Promethium, Samarium, Europium, Gadolinium, Terbium, Dysprosium, Holmium, Erbium, Thulium, Ytterbium, Lutetium), Yttrium, Scandium and Boron, and the applications of this method.

24 Claims, 4 Drawing Sheets

(56) References Cited

OTHER PUBLICATIONS

Hossein Janshekar et al. "biomass conversion : emerging technologies, feedstocks, and products; SRI Biotechnology-Based Chemicals"; SRI consulting report, Chemical Building Blocks From Renewables, Marifaith Hackett, Sep. 2011; pp. 1-36.
J.A. Diaz-Guillen et al., "A rapid method to obtain nanometric particles of rhabdophane LaPO4 nH2O by mechanical milling" Journal of Alloys and Compounds; 2007; vol. 427 pp. 87-93.
Jia Ouyang et al., Catal. Lett.; 2009; vol. 132; pp. 64-74.
Kanaparthi Ramesh et al., Structure and reactivity of phosphorous modified H-ZSM-5 catalysts for ethanol dehydration; Catalysis Communications; 2009; vol. 10 pp. 567-571.
Komban Rajesh et al. "A Facile Sol-Gel Strategy for the Synthesis of Rod-Shaped, Nanocrystalline, High-Surface-Area Lanthanum Phosphate Powders and Nanocoatings" Advanced Functional Materials; 2007; vol. 17; pp. 1682-1690.
Mansoor Anbia et al. "Humidity Sensing Properties of the Sensor Based on V-doped Nanoporous Ti0.9Sn0.1O. Thin Film" Chinese Journal Chem.; 2012; vol. 30; pp. 842-846.
Mansur Anbia, et al. "Synthesis of Mesoporous Lanthanum Phosphate and Its Use as Novel Sorbent" Chinese Journal of Chemistry; 2006; vol. 24; pp. 1026-1030.
Paul Brandao et al., "Dehydration of alcohols by microporous niobium silicate AM-11" Catalysis Letters; Jun. 3-4, 2002; vol. 80; pp. 99-103.
Report EPA/600/R-07/144, Dec. 2007.
T.M. Nguyen et al., "Conversion of Ethanol in Aqueous Solution over ZSM-5 Zoelites, Study of the Reaction Network" Applied Catalysis; 1990; vol. 58; pp. 119-129.
Thomas R. Harris et al. "Economic Analysis of Waste Recycling Options for Washoe Country" Technical Report UCED; Center for Economic Developement; Nov. 9, 2011; pp. 1-76.
Vishnu Menon et al. "Trends in bioconversion of lignocellulose: Biofuels, platform chemicals & biorefinery concept" Progress in Energy and Combustion Science; 2012; vol. 38; pp. 522-550.
Werner H. Baur et al. "A historical note on the sodalite framework: The contribution of Frans Maurits Jaeger" Microporous and Mesoporous Materials; 2008; vol. 116; pp. 1-3.
Xiang Zhang et al., "Comparison of four catalysts in the catalytic dehydration of ethanol to ethylene" Microporous and Mesoporous Materials; 2008; vol. 116; 210-215.
Nina Zhan et al. "Lanthanum-phosphorous modified HZSM-5 catalysts in dehydration of ethanol to ethylene: A comparative analysis", Catalysis Communications; 2010; vol. 11; pp. 633-637.
S. S. Jewur et al. "The role of surface acidity of boron phosphate in the activity and selectivity of the dehydration of alcohols", Journal of Catalysis, 1979, vol. 57, pp. 167-176.

* cited by examiner

METHOD FOR PRODUCING AN OLEFIN BY CATALYTIC CONVERSION OF AT LEAST ONE ALCOHOL

The present invention relates to a catalytic method for producing olefines, dienes, polyenes by dehydration of alcohols.

Olefines, also called ethylenic hydrocarbons or alkenes, consist of hydrocarbons of the general formula $C_nH_{2n}$ with n larger than or equal to 2. Dienes and polyenes consist of hydrocarbons the molecule of which comprises two ethylenic bonds or more. This general definition applies to any hydrocarbon having one or several ethylenic bonds and including any function, such as for example, primary, secondary and tertiary amino groups, primary, secondary and tertiary alcohol groups, carbonyl groups of which aldehyde groups, . . . , conjugated or not with the or one of said ethylenic bond(s).

Light olefines, such as ethylene, propene and butenes, as well as butadiene, are major hydrocarbon raw materials for the chemical syntheses and for the petrochemical industry. The numerous addition reactions that they can undergo place them at the center of a set of large tonnage industries for production of functional intermediates. For example, ethylene will oxidize into epoxyethane (ethylene oxide) or constitute a source of glycol, ethanolamines, glycol ethers and esters, or it will oxidize into ethanal (acetaldehyde), chlorinate and dehydrochlorinate into vinyl chloride, be added to benzene and then dehydrogenate into styrene, or even, polymerize into polyethylene. Propene allows accessing a large variety of petrochemical products such as polypropene, acrolein, acrylonitrile, cumene, oxo alcohols (butanol, 2-ethyl-butanol, 2-ethyl-hexanol), propene oxide, acrylic acid, isopropyl alcohol, and polygas chemical products. Used as a synthon in the alkylation units, the catalytic polymerization units, and the dimerization units, it allows producing mixtures of gasolines with a high octane rating. Propene and butenes are also transformed into functional intermediate products. Their polymerizations and copolymerizations result in macromolecules which have remarkable practical properties. Isobutylene, also known as isobutene or 2-methylpropene, constitutes a starting monomer for butyl rubber (a copolymer of isobutylene and small amounts of isoprene). Isoprene, also known as 2-methylbut-1,3-diene or terpene, is the precursor of the synthetic rubber (polyisoprene), styrene-isoprene-styrene block copolymers, and butyl rubber. Buta-1,3-diene, often directly called butadiene, is mainly used in the manufacture of synthetic rubber, varnish, nylon and (botanical) latex paints. A large number of car tires are manufactured with buna rubber, which is a copolymer of butadiene and styrene. Butadiene also constitutes the main reactant for the synthesis of chloroprene by chlorination followed with isomerization and dehydrochlorination. This diene is also used to produce adiponitrile and hexamethylenadiamine by reaction with hydrocyanic acid. Several methods use butadiene to produce butan-1,4-diol. Butadiene is an excellent reactant for the Diels-Alder reaction and it allows the synthesis of 4-vinylcyclohexene (a reactant for the production of styrene), 1,5-cyclooctadiene and 1,5,9-cyclodecatriène.

At present, these synthetic raw and intermediate materials are obtained mainly from fossil fuels by steam cracking, catalytic cracking, catalytic dehydrogenation and metathesis. These methods consume a lot of energy and emit a lot of $CO_2$, which is a greenhouse gas.

Ethylene, which constitutes the pillar of the global chemical industry, comes primarily from steam cracking liquid petroleum products (naphtha or gasoil) or natural gas liquids (ethane, propane and butane) where it is accompanied by its first homologues:propene or propylene, but-1-ene and cis and trans but-2-enes, isobutylene and but-1,3-diene, and from which it is separated by fractional distillation.

Like ethylene, propene constitutes a cornerstone of the petrochemical industry. Nowadays, propene comes exclusively from fossil fuels. It consists of the major co-product in the production of ethylene by thermal cracking. The steam cracking units of naphtha or gasoil are more selective to propene than those which use the liquefied petroleum gas as a raw material. Oil refineries also generate significant amounts of propene as a sub-product of the fracturing, coking and visbreaking catalytic operations. Propene may also be obtained by catalytic dehydrogenation of propane or by metathesis of ethylene and but-2-enes.

Dienes and polyenes are very rarely found in the natural state. One of the simplest dienes is isoprene, $CH_2=C(CH_3)—CH=CH_2$, which results from the pyrolysis of several natural terpenes and polyterpenes. The others are accessible through numerous syntheses. Butadiene, which appears when cracking hydrocarbons (5% of butadiene is produced in the cracking of light gasolines), is separated from the mixture by distillation of the $C_4$ fractions. Obtaining pure butadiene is not possible by simple distillation of this fraction, as butane and butadiene form an azeotrope. This separation generally requires performing a liquid-liquid extraction or an extractive distillation. Butadiene is also industrially synthesized by dehydrogenation of butane, or mixtures of butenes and butane.

Recent technological developments predict a more and more significant availability, in the short term, of pure or mixed alcohols, capable of reducing the dependence on fossil fuels and alleviating the harm to the environment, in particular in terms of carbon dioxide emissions (see the report EPA/600/R-07/144, Décembre 2007, biomass conversion: emerging technologies, feedstocks, and products; SRI BIOTECHNOLOGY-BASED CHEMICALS by Hossein Janshekar, KazuteruYokose, Marifaith Hackett, and Xiaomeng Ma, SRI consulting report, CHEMICAL BUILDING BLOCKS FROM RENEWABLES, Marifaith Hackett, September 2011).

Methanol is produced commercially by reacting the synthetic gas under pressure and in the presence of a catalyst (see CEH Marketing Research Report, METHANOL, Guillermo A. Saade, June 2009). The synthetic gas is a mixture of gases which is composed mainly of carbon oxide and hydrogen, with small amounts of carbon dioxide and other gases. It is mainly produced from natural gas but also from other sources of hydrocarbons (naphtha, oil residues, coal residues and, at least potentially, gases from landfill sites which contain methane). In order to limit the production costs of methanol, numerous industrial sites increase their production capacities in order to benefit from the positive impact of the scale effect, whereas others direct their researches on the one-step reaction of methane and oxygen without intermediate formation of the synthetic gas.

All products that come from biomass, regardless of their origin, allow producing, whether directly or as sub-products, whether by fermentation or by a chemical process, functionalized chemical compounds such as $C_6$, $C_5$ and $C_4$ alcohols, diols, polyols, and even $C_1$, $C_2$ and $C_3$ synthons. In particular, renewed interest may be noticed for the bio-based butanediol, including butane-1,4-diol and butane-2,3-diol. A recent report, published by the American cabinet Transparency Market Research, tends to demonstrate that the bio-based butane-2,3-diol is about to replace its fossil-derived version. This diol could offer a clean alternative solution at competitive costs. One of the largest applications of the bio-based butane-2,3-diol remains the production of buta-1,3-diene, which is a raw material in rapid growth. Another particularly known example is ethanol which remains mainly produced by fermentation of a carbohydrate (starch, sugar or cellulose), followed by a distillation and treatments appropriate for its final use (fuel, solvent, chemical raw materials . . . ). Thus, it is commercially available, in a pure form (99.9% anhydrous ethanol) or in an aqueous solution at a concentration higher than 80%. Many researches focus on the development of methods which allow producing ethanol at low cost from non-food raw materials. This is particularly the case of cellulosic ethanol (see CEH Marketing Research Report, ETHANOL, Eric Linak, Hossein Janshekar and Yoshio Inoguchi, April 2009).

The ABE (Acetone-butanol-ethanol) fermentation consists of a method that uses the bacterial fermentation to produce acetone, n-butanol and ethanol from starch. The industrial exploitation of this ABE fermentation started in 1916 when Chaim Weizmann isolated the *Clostridium acetobutylicum bacterium*, as described in U.S. Pat. No. 1,315,585A. The method produces mixtures of acetone, n-butanol and ethanol with ratios ranging around 3-6-1. The raw material and the strain that are used have a direct influence on the composition of the mixture at the outlet of the fermentation reactor. Thus, for example, Cobalt Technologies, Inc. claims, in its patent application US2010330633A1, having achieved a 80% yield of butanol from fermentation of sucrose and *Clostridium saccharubutylium*, whereas Lanzatech New Zealand LTD claims, in its U.S. Pat. No. 8,119,844B2, having achieved a 63% yield from fermentation of glycerol and *Clostridium pasteurianum*. In order to make the ABE fermentation profitable, numerous systems for recovering products in-situ have been developed. In particular, they involve distillation, pervaporative separation, membrane extraction, adsorption and reverse osmosis. A further more relevant valorization would aim to directly exploit the obtained mixture.

The European Directives 2001/77/EC and 2003/30/EC, which will enter into application in the near future, plan to introduce 10% of Diester® (or VOME, methyl esters of vegetable oils) in gasoils by 2015. This biodiesel is produced by transesterification, by methanol, of the triglycerides that are contained in the oleaginous liquids, in particular in the palm, rapeseed and sunflower vegetable oils. Depending on the considered methods, about 100 kg of glycerol per ton of Diester® are produced as a co-product of the reaction. The substantial increase of the amount of biodiesel which will be produced during the next years will generate significant amounts of glycerol equivalent to several hundreds of thousands of tons per year. In general, glycerol produced in this manner has a purity of 75-90%. Water and residual salts (often coming from the catalysts) are the main contaminants of this glycerol. Depending on the intended application, it will be more or less refined. Some 1500 uses of glycerol have already been identified, among which, the following by way of examples illustrate its presence in numerous and various formulations:

moisturizers for pharmaceutical use (in suppositories and syrups) or for cosmetic use in moisturizing creams, glycerin soaps, toothpastes,
  solvents in the food industry,
  plasticizers and lubricants in the chemical industry.

These applications will prove to be clearly insufficient for absorbing the amounts of glycerol that will be produced with the biodiesels, and although the conventional market of glycerol (soaps, pharmaceutics . . . ) is in progression, it will not be capable of absorbing such a surplus. Therefore, it is essential to find new applications which allow benefiting from large volumes of glycerol. With this in mind, numerous possibilities have been studied the last few years (see M. Pagliaro, M. Rossi: The Future of Glycerol, RSC Publishing, Cambridge (2008)), in particular, with the conversion into propane-1,3-diol and propane-1,2-diol which are used, in particular, as base monomers in the synthesis of polyesters and polyurethanes.

Dupont and Tate & Lyle have developed a biofermental process which allows producing propane-1,3-diol (an enzyme co-developed with Genencor (Danisco)) from corn starch, without necessarily going through glycerol.

Considering the recent developments which should facilitate access to numerous alcohols, renewed interest is observed for the very ancient Guerbet reaction. This reaction allows obtaining alcohols from shorter alcohols by means of an acid-base catalyst. In U.S. Pat. No. 7,807,857B2, Dupont proposes a method for obtaining Guerbet alcohols (butanol and higher alcohols) from ethanol. In U.S. Pat. No. 7,989,664B2, Virent Energy Systems describes a method for obtaining polyols which may include alcohols such as methanol, ethanol, isopropyl alcohol, propanol, butanol, pentanol and hexanol. In its U.S. Pat. No. 8,187,347B2, Kabushiki Kaisha Sangi proposes a method which allows obtaining a mixture of alcohols and olefines from alcohols, and in its U.S. Pat. No. 8,080,695B2, it describes a method for obtaining a mixture of butan-1-ol, hexanol, octanol and decanol from ethanol.

It should be pointed out that the biomass transformation does not constitute the only way for producing alcohols in large amounts. Thus, the syngas methods are modified so as to result in alcohols others than methanol, such as ethanol, propan-1-ol and propan-2-ol and butanols. The catalysts are metal based, such as Cu, Zn, Mo or Cr, doped with alkali metals. Methods for producing mixtures of alcohols other than methanol have thus been developed by the Snamprogetti, Topsoe, Lurgi, Dow and IFP-Idemitsu companies. The reactions that are involved in these methods include the water-gas shift reaction, the beta co-addition, homologations of ethanol and other longer alcohols, condensation, dehydration, formation of branched iso-alcohols and methyl esters.

Thus, some alcohols, such as, for example, methanol, ethanol and butanol, have already been produced industrially at large scale. The technologies of the future will allow access to these alcohols and to many other alcohols, whether pure or mixed, at low cost. With the increasing demand for olefine, the depletion of conventional fossil raw materials and the development of access to alternative raw materials, the selective dehydration of alcohols into olefines appears to be a promising alternative industrial process, especially as it will be capable of treating mixtures of alcohols.

As a general rule, the hydration reactions are favored at low temperature whereas the dehydration reactions are favored at high temperature. In order to obtain the desired dehydration products, it is therefore necessary to apply a sufficient reaction temperature, and/or a partial vacuum in order to shift the equilibrium of the reaction. The dehydration reaction may be carried out in a liquid phase or in a gas phase. This type of reaction is known to be catalyzed by inorganic acids or by acid solids.

Many acid catalysts are effective in the dehydration of ethanol. Most of these catalysts are based on doped alumina, supported phosphoric acid, silica-aluminas or zeolites (see A. Morschbacker, Journal of Macromolecular Science, Part C: Polymer Reviews, 49 (2009) 79-84; O. Winter, E. Ming-Teck, Hydrocarb. Process November (1976) 125-133; C. B. Phillips, R. Datta, Ind. Eng. Chem. Res. 36 (1997) 4466-4475; T. M. Nguyen, R. L. V. Mao, Appl. Catal. 58 (1990) 119-129, X. Zhang, R. Wang, X. Yang, F. Zhang, Micro and Meso Materials 116 (2008) 210-215.). Almost all of the first industrial catalysts that have been proposed have been based on supported phosphoric acid but they have rapidly been replaced by aluminas or silica-aluminas because of their higher productivity and the absence of inherent corrosion in their use.

Nonetheless, these catalysts require high reaction temperatures (430-450° C.) and they are less effective when the alcohol solutions contain large amounts of water. For these reasons, synthetic zeolites such as the HZSM5 have been developed as catalysts [see C. B. Phillips, R. Datta, Ind. Eng. Chem. Res. 36 (1997) 4466-4475 et T. M. Nguyen, R. L. V. Mao, Appl. Catal. 58 (1990) 119-129]. They have been used only for the dehydration of ethanol and they allow lowering the temperature of reaction (300° C.) without any loss of effectiveness (for example, a selectivity of 95% to ethylene for a conversion of ethanol of 98% may be obtained on a HZSM55-based catalyst). SAPO-34 type zeolites have also been used successfully. However, the dehydration of the alcohols takes place on the acid sites which are weak or of medium strength of the catalyst and the presence of non-uniformly distributed strong acid sites, as is the case in these zeolitic materials, causes the formation of undesirable products and a significant coke formation on the catalyst (see X. Zhang, R. Wang, X. Yang, F. Zhang, Micro and Meso Materials 116 (2008) 210-215). Therefore, the zeolites have to be modified by doping with phosphor (see D. S. Zhang, R. J. Wang, X. X. Yang, Catal. Lett. 124 (2008) 384-391 et K. Ramesh, L. M. Hui, Y. F. Han, A. Borgna, Catal. Commun. 10 (2009) 567-571), rare earth metals (see J. Ouyang, F. X. Kong, G. D. Su, Y. C. Hu, Q. L. Song, Catal. Lett. 132 (2009) 64-72; U.S. Pat. No. 4,873,392A; N. Zhan, Y. Hu, H. Li, D. Yu, Y. Han, H. Huang, Catal. Comm. 11 (2010) 633-637), or still, as is the case with the SAPO-34, by nickel (see X. Zhang, R. Wang, X. Yang, F. Zhang, Micro and Meso Materials 116 (2008) 210-215), in order to eliminate the overly strong acid sites and increase the number of moderately strong or even weak acid sites.

These modifications improve the selectivity and the stability of the catalysts, but nonetheless, have a drawback related to the necessity of using a relatively low weight hourly space velocity.

While the dehydration of propanol-2 is commonly used to characterize the acidity of all types of catalysts, the dehydration of n-propanol has not been sufficiently studied. The best catalysts that have been obtained give a yield of 100% at 380° C. (see P. Brandao, A. Philippou, J. Rocha, M. W. Anderson, Catal. Letters 80 (2002) 99) on zeolite-based catalysts.

Research on the production of butanol by fermentation has intensified these last few years and significant advances have been made. These advances relate to, at the same time, the microbial strains and the fermentation technology, the quality of the starting products which may consist of biomass residues and the techniques used for the separation of the obtained products [A. P. Mariano, R. MacielFilho, J. Bioenerg. Res. 5 (2012) 504. Et V. Menon, M. Rao, Progress in Energy and Combustion Science 38 (2012) 522]. Bio-butanol is now considered to be a possible biofuel because it can be produced on a scale of millions of tons.

Many applications have been developed to benefit from this bio-butanol. It may be catalytically dehydrogenated or dehydrated. In the first case, butanone (or methylethylketone), which is a common solvent in the chemical industry, is produced [C. F. Turner, J. W. McCreery, The Chemistry of Fire and Hazardous Materials. Boston, Mass.: Allyn and Bacon, Inc. (1981) 118.]. In the second case, the different isomers of butene (but-1-ene, cis-but-2-ene, trans-but-2-ene and isobutene) are produced. The distribution of these different butenes depends on the starting alcohol (butan-1-ol, butan-2-ol and isobutanol), the temperature (thermodynamic equilibrium) and the catalyst. Butenes are used in the production of plastics such as but-1-ene or lubricants such as but-2-ene or gums (butyl rubber) and methyl tert-butyl ether (MTBE), or iso-octane such as isobutene.

But-2-ene may also be used to produce propene by metathesis reaction with ethylene. This metathesis production is expected to be developed in the near future since it offers access to fully bio-based propene. Nonetheless, since the main product of most methods for producing butanol by fermentation is butan-1-ol, the butene that is necessary for the metathesis reaction is but-2-ene. Therefore, it is important to provide a catalytic method for selective conversion of butan-1-ol into but-2-enes. To our knowledge, a catalyst that allows obtaining an acceptable selectivity has not yet been reported.

A fundamental scientific advance would consist in developing a catalyst that allows the selective dehydration of butan-1-ol into but-2-ene in combination with the selective dehydration of ethanol into ethylene, this catalyst being capable of being used to selectively convert the two alcohols at the same temperature. In addition, if the catalyst was also selective for converting butan-2-ol into but-2-enes, it would be no longer necessary to separate the alcohols or enrich the reaction with either one of them. The dehydration of the mixture of alcohols could be carried out in one single step and result directly in an optimum mixture for the metathesis reaction.

If there is any particular interest in converting ethanol and butanol simultaneously on the same catalyst, it may also be interesting to convert other mixtures of binary or more complex alcohols simultaneously on the same catalyst, at the same temperature, in order to obtain, rather selectively, a mixture of alkenes while avoiding any parasitic cracking or ether formation reactions. The catalyst that is used in such a reaction should be quite active and selective in order to dehydrate all the considered alcohols at the same temperature range.

The object of the present invention consists in implementing catalysts that are robust, active, selective and regenerable, and which allow the production of olefines, dienes and/or polyenes from alcohols, diols, polyols, whether pure or mixed, according to a dehydration reaction. The inventors of the present invention have developed highly selective, regenerable and active catalysts at a lower temperature than the catalysts that have been described in the prior art for the dehydration of alcohols.

Thus, the invention relates to a method for preparing one or several olefines, dienes or polyenes, by catalytic conversion of at least one alcohol having a carbon chain of at least three carbon atoms and different from propan-2-ol, in the presence of at least one catalyst based of at least one phosphate of a metal or several metals M, M chosen from among the 15 lanthanides (Lanthanum, Cerium, Praseodymium, Neodymium, Promethium, Samarium, Europium, Gadolinium, Terbium, Dysprosium, Holmium, Erbium, Thulium, Ytterbium, Lutetium), Yttrium, Scandium and Boron.

By alcohol, it is meant, according to the present invention, a hydrocarbon chain whether saturated or unsaturated, linear or branched, which carries one or several hydroxyl groups, such as diols and all other polyols.

Hereinafter, the present invention is described in more detail, highlighting the variants and advantages of the method of the invention, as well as its applications.

Preferably, the catalyst is based of at least one phosphate of one or several metals M chosen from among Lanthanum, Praseodymium, Neodymium, Promethium, Samarium, Europium, Gadolinium, Terbium, Dysprosium, Holmium, Erbium, Thulium, Ytterbium, Lutetium, Yttrium and Scandium.

According to a still preferred implementation, the catalyst is based of at least one phosphate of one or several metals M chosen from among Lanthanum, Neodymium, Gadolinium and Samarium.

The catalyst of the invention may be doped by at least one alkali metal chosen from among Cesium, Rubidium and Potassium and/or a transition metal chosen from among groups 4 to 7.

Advantageously, the molar ratio P/M varies from 0.5 to 2, and better still from 0.9 to 1.5, M representing the metal or the sum of the metals M which constitute said catalyst.

The method of the invention has a major interest consisting in that it allows treating one or more alcohols, whether pure, partially purified, unpurified or in the form of azeotropic compositions, as well as any mixture of these. They may be treated in an inert gas, whether or not in the presence of an oxidant gas ($O_2$, $H_2O$, $CO_2$, $O_3$ ... ). The presence of such a gas allows improving the stability of the catalyst over time. The alcohol(s) may be in an aqueous solution, preferably at a concentration of at least 1% weight.

Because of their availability and/or the product that results from their dehydration, preferred alcohols are chosen among propan-1-ol, butan-1-ol, butan-2-ol, isobutanol, but-3-ene-1-ol, but-2-ene-1-ol, but-3-ene-1,2-diol, butane-2,3-diol, butane-1,3-diol, butane-1,4-diol, glycerol, propane-1,2-diol, propane-1,3-diol, erythritol, and their mixtures.

According to the invention, prepared olefine, diene or polyene has a carbon chain of the same number of carbon atoms as the alcohol(s) from which they have been prepared; thus, an object of the invention is a method for preparing at least one olefine, diene or polyene having a carbon chain of at least three carbon atoms and which are obtained by catalytic conversion of an alcohol or a mixture of corresponding alcohols, having a carbon chain of the same number of carbon atoms.

Another interesting object of the invention consists in implementing the above-described method for preparing a mixture of olefines, dienes and/or polyenes.

More specifically, it allows preparing a mixture of at least two olefines, dienes and/or polyenes, from at least one alcohol having a carbon chain of at least three carbon atoms and different from propan-2-ol. According to a variant of the invention, the method allows preparing a mixture of at least two olefines, dienes and/or polyenes, from among a mixture of alcohols comprising at least one alcohol having a carbon chain of at least three carbon atoms and different from propan-2-ol, and any other alcohol.

Thus, another object of the invention is a method for preparing a mixture of at least two olefines, dienes and/or polyenes, according to which at least one of the olefines, dienes and/or polyenes is prepared by a method of the invention. The at least other olefine(s), diene(s) and/or polyene(s) may or may not be obtained by a method of the invention; they may be obtained by catalytic conversion of an alcohol or a mixture of alcohols, in the presence of at least one catalyst, as previously defined.

Preparation of said olefines, dienes and/or polyenes, may be carried out by catalytic conversion of an alcohol or a mixture of alcohols, in the presence of the same catalyst or in the presence of different catalysts.

They may be prepared in the same reactor, in the presence of the same catalyst or in the presence of different catalysts; they may also be produced in different reactors, in the presence of an identical catalyst or of different catalysts.

The catalysts of the invention have proven to be capable of selectively transforming several alcohols while these alcohols are mixed.

Advantageously, said catalyst(s), which are used for the preparation of these olefines/dienes/polyenes, comprise an active phase and a support and/or a binder. They may also be formed, optionally in the presence of a binder. They may also be regenerated.

Pure or mixed alcohols may be treated in an inert gas, whether or not in the presence of an oxidant gas ($O_2$, $H_2O$, $CO_2$, $O_3$ ... ). The presence of such a gas allows improving the stability of the catalyst over time.

In comparison with the prior art, the described invention provides a method for preparing C4 olefines which is more active and more selective in but-2-ene than in but-1-ene by catalytic dehydration of $C_4$ alcohols in the presence of a catalyst which, while allowing for total conversion of the starting $C_4$ alcohol, may be regenerated very easily and has a long lifespan. The reaction may be carried out in a liquid phase, in a gas phase or in a biphasic mixed medium.

In the case of a reaction in a gas phase, after dehydration, the reaction gas is cooled in a water quench column, which separates the major part of the products from the water and alcohol which did not react. The subsequent treatment of the flow of olefine, diene and/or polyene depends on the purity level that is required from the final product, in particular, according to the expected use.

Thus, this alternative allows for a competitive method for synthesizing olefines, dienes and/or polyenes or ketones which is less dependent on conventional fossil resources, while alleviating the harm to the environment. The recent technological and biotechnological developments promise an increased availability, in the short term, of pure or mixed alcohols. These scientific developments would allow for decreases of the harm to the environment by reducing the emissions of greenhouse gases, in particular carbon dioxide.

Hereinafter, examples of fundamentally interesting applications of a method of the invention are disclosed:

The selective preparation of but-2-ene from butan-1-ol, butan-2-ol and their mixtures;

The production of propene, by implementing any one of the following methods:
- Preparation of propene by a method according to the invention, wherein the alcohol is chosen from among propan-1-ol, optionally mixed with propan-2-ol;
- Preparation of a butene by a method according to the invention, wherein the alcohol is chosen from among butan-1-ol, butan-2-ol and their mixtures, and then conversion of the butene into propene by metathesis;
- Preparation of a mixture of ethylene and butene by a method according to the invention, wherein at least one alcohol consists of ethanol and another alcohol is chosen from among butan-1-ol, butan-2-ol and their mixtures, and then conversion of the mixture of ethylene and butene into propene by metathesis.

The production of butadiene, by implementing a method of the invention, wherein the alcohol is chosen from among but-2-ene-1-ol, but-3-ene-1-ol, but-1-ene-3-ol, but-3-ene-1,2-diol, butane-2,4-diol, butane-2,3-diol, butane-1,3-diol, and butane-1,4-diol and their mixtures;

The production of isobutene from isobutanol;

The production of pentene and isoprene from alcohols, in particular from the corresponding diols;

The production of acrolein, acrylic acid, acrylonitrile and polypropylene from propene that has been produced according to the present invention;

The production of the aldehyde-3-(methylthio)propionic acid (MMP), the 2-hydroxy-4-methylthiobutyronitrile acid (HMTBN), methionine, the 2-hydroxy-4-methylthiobutyric acid (HMTBA), esters of these molecules, or the 2-oxo-4-methylthiobutanoic acid (KMB), from acrolein, produced as described above, or from propene.

Methionine, HMTBA and the esters of the latter and analogues, are used for animal nutrition and, in their industrial synthetic methods, acrolein is generally obtained by oxidation of propene and/or propane. The oxidation of propene into acrolein by air in the presence of water is partial, and the resulting crude product, which is acrolein based, also contains propene and propane that have not reacted, water and sub-products of the oxidation reaction, in particular acids, aldehydes and alcohols.

Conventionally, acrolein and acrylic acid are produced by controlled oxidation of propene by atmospheric oxygen in a gas phase in the presence of catalysts based on molybdenum and/or bismuth oxides. The acrolein that is obtained in this manner may be either directly integrated in a method for producing acrylic acid, acrylonitrile, or used as a synthesis intermediate.

The markets of acrolein, which is one of the simplest unsaturated aldehydes, acrylonitrile and acrylic acid are colossal since these monomers enter into the composition of numerous mass-market products.

Moreover, acrolein, which is a highly reactive compound because of its structure, has numerous applications, in particular as a synthesis intermediate. As previously said, it is quite particularly used as a key intermediate involved in the synthesis of D,L-methionine and its analogous hydroxy derivative, the 2-hydroxy-4-methylthiobutyric acid (HMTBA). These feed additives are massively used since they enter into the composition of feed supplements that are essential for animal growth (poultry, pigs, ruminants, fish . . . ).

In some cases, it may be profitable to be able to increase, and even ensure, the production capabilities of existing industrial units by diversifying the used raw material. Therefore, it appears to be particularly interesting to be able to increase the acrolein productivity, while reducing the dependence with respect to this oil-based resource which is propene, and alleviate the harm to the environment. Thus, propene may be obtained by metathesis of ethylene and n-butenes, obtained separately or as mixtures by dehydration of alcohols or directly by dehydration of propan-1-ol, also called n-propanol, or by cracking higher olefines.

Obtaining propene by metathesis of ethylene and n-butenes may be summarized according to the following balanced equation:

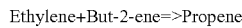
Ethylene+But-2-ene=>Propene

This reaction is thermodynamically favored but it is balanced. The use of an excess of ethylene allows promoting the formation of propene. This reaction remains selective but requires the absence of all organic impurities. Therefore, a prior purification of the reactants is to be ensured, otherwise, the reaction should be carried out from highly purified reactants. This reaction is only effective with but-2-ene. A parasitic reaction between two molecules of but-1-ene would result in hex-3-ene and ethylene. Therefore, it is necessary to either add an isomerization reactor which transforms the non-reactive but-1-ene into part but-2-ene, or to use a fraction that has been enriched beforehand with but-2-ene. Producing propene with a good selectivity and with a good rate of progress is promoted by an excess of but-2-ene with respect to but-1-ene and with an excess of ethylene. For example, the patent application US2005/0124839A1, in the name of LUMMUS, recommends proceeding with a molar ratio of reactants «ethylene/sum of butenes» comprised between 0.9 and 2. The Meta-4 method of IFP proposes a continuous method for producing propene from ethylene and but-2-ene by metathesis at low temperature in a liquid phase in the presence of a heterogeneous Rhenium-based catalyst (see U.S. Pat. No. 6,075,173A). At equilibrium, a conversion rate of 63% at 35° C. is announced.

A highly advantageous application of the invention consists of the synthesis of a fraction which is enriched with but-2-ene or a flow which promotes the selective production of propene by metathesis of ethylene and butene.

In comparison with the prior art, the described invention provides a method for preparing $C_4$ olefines which is more selective to but-2-ene than to but-1-ene and which involves a catalytic dehydration of $C_4$ alcohols in the presence of a catalyst which, while allowing for total conversion of the starting $C_4$ alcohol, may be regenerated quite easily and has a significant lifespan.

Similarly, according to the described invention, it is possible to obtain a mixture of ethylene and butenes, which promote the production of propene by metathesis, by catalytic dehydration of a mixture of ethanol and a $C_4$ alcohol, and preferably by butan-1-ol.

The catalyst may be prepared in various ways (coprecipitation, hydrothermal synthesis . . . ), well known by those skilled in the art. In particular, those skilled in the art may refer to the following articles, M. Anbia, M. K. Rofouel, S. W. Husain, Chin. J. Chem. 24 (2006) 1026-1030; J. A. Diaz-Guillen, A. F. Fuentes, S. Gallini, M. T. Colomer, J. Alloys and Compounds 427 (2007) 87-93; K. Rajesh, P. Shajesh, O. Seidel, P. Mukundan, K. G. K. Warrier, Adv. Funct. Mater. 17 (2007) 1682-1690.

The initial phosphor precursor may be chosen from among several compounds such as ammonium phosphates and ammonium hydrogenphosphates, alkali phosphates and preferably sodium phosphates, phosphoric acids and preferably orthophosphoric acids, the anhydride phosphor oxide or the organic compounds of phosphor such as phosphoric ethers.

Furthermore, the catalyst that has been previously defined may comply with the preferred characteristics which follow, considered alone or in combination:

the catalysts are mainly constituted by phosphates and mixed phosphates, as previously defined, which constitute the main active phase(s) of the catalysts.

the catalysts are mainly composed of an orthophosphate phase, whether pure or in a mixture.

the molar ratio P/M varies from 0.5 to 2, more advantageously, it varies from 0.9 to 1.5, M representing the metal or the sum of the metals M which constitute said catalyst.

Said catalyst may also comprise the phosphate-based active phase and at least one binder or support for this active phase. The support or the binder may be constituted by pure silica ($SiO_2$), a silicate (a silica of an alkali metal, of an alkaline earth metal or of rare earth metals) possibly mixed together or with clays, titanium oxide (TiO$_2$), boron oxide (B$_2$O$_3$) or resins (sulphonic resins, perfluorosulfonicresins or others). The preferred binders or supports are silica based, in all forms that are known by those skilled in the art, titanium oxide based and their mixtures. The weight content of the binder or support in the catalyst is comprised between 0 and 80%, more particularly between 5% and 50%.

The support may be prepared by forming, whether or not in the presence of a binder, by any technique known by those skilled in the art. For example, forming may be carried out by extrusion, by pelletization, by the drop coagulation method (oil-drop), by turntable granulation or by any other method well known by those skilled in the art. At least one calcination may be performed after any one of the preparation steps, it is usually performed in air at a temperature of at least 150° C., preferably at least 300° C.

As previously said, the catalyst of the invention is interesting in that it can be easily regenerated, and thus without affecting the yield of the dehydration, nor the selectivity to the obtained olefine, diene and polyene, respectively. For example, this regeneration is performed by air, diluted air, enriched air, in situ or ex situ. Advantageously, it takes place in situ.

The reaction according to the invention may be implemented in a gas phase or in a liquid phase, and preferably in a gas phase. In the case where the reaction is carried out in a gas phase, different method technologies may be used, namely a fixed bed method, a fluidized bed method or a circulating fluidized bed method, for example in a TZFBR reactor (two zone fluidized bed reactor). In the first two methods, that is to say the fixed bed method or the fluidized bed method, the catalyst regeneration may be separated from the catalytic reaction. For example, it may be carried out ex situ by conventional regeneration methods, such as combustion in air or with a gaseous mixture containing molecular oxygen or any other oxidant. According to the method of the invention, the regeneration may be carried out in situ as the temperatures and pressures, under which the regeneration is carried out, are compatible with the reaction conditions of the method.

In addition to this regeneration which aims primarily to eliminate the coke that has been formed at the surface of the catalysts, a continuous or discontinuous regeneration of the catalyst may be carried out in order to reinforce the long-term stability and generate an optimum molar ratio phosphor/rare earth metals (RE). For this purpose, the catalyst may be brought into contact with a phosphor-based compound which has been added to the reactants during the catalytic reaction, the regeneration or during a dedicated step. By way of examples, appropriate phosphor-based compounds are chosen from among triethyl phosphate or other alkyl phosphates such as trimethyl phosphate, phosphites such as trimethylphosphite and triethylphosphite, and other phosphines. These compounds may be added with or without water; still the presence of some water is preferable.

Since it consists of the liquid-phase method, the reaction may be carried out in a conventional reactor used for reactions in a liquid phase on a solid catalyst. Nonetheless, considering the significant difference between the boiling points of the alcohols and those of the corresponding olefines, dienes and polyenes, the reaction may also be carried out in a reactor used for catalytic distillations. Besides, it is also reasonable to consider a liquid-phase method at a relatively low temperature which allows a continuous distillation of the obtained products, thereby limiting consecutive degradation reactions.

Preferably, the experimental conditions of the gas-phase reaction consist of a temperature comprised between 150 and 450° C. at a pressure comprised between 1 and 10 bars. In a liquid phase, the reaction is carried out at a temperature between 50 and 200° C. and at a pressure which may range from 3 to 70 bars.

Another advantage of the method of the invention lies in the form of the starting alcohols which may be pure, partially purified or in a solution, in particular in an aqueous solution or in mixtures. Furthermore, the solutions of alcohols should not be over diluted, due to the prohibitive energy cost that would result from the evaporation of the alcohols. In all cases, it is practical to adjust the concentration of the alcohol solution by partially or totally recycling the water that has been produced by the considered reaction. It is possible to optimize the energy consumption through the synthesis by recovering heat at the reactor outlet and use it to vaporize the alcohol(s) flow that feeds the reactor. Thus, in the rest of the description, reference will be primarily made to the conversion of a pure alcohol or a mixture of alcohols, regardless of their origins and degrees of purity.

Depending on the considered application, it is possible to consider purifying the olefines, dienes and polyenes or the mixture of olefines, dienes and/or polyenes that have been obtained by conventional techniques known by those skilled in the art.

Another object of the invention is a method for producing the aldehyde-3-(methylthio)propionic acid (MMP), the 2-hydroxy-4-methylthiobutyronitrile acid (HMTBN), methionine, the 2-hydroxy-4-methylthiobutyric acid (HMTBA), esters of the latter, in particular the isopropyl ester, and the 2-oxo-4-methylthiobutanoic acid (KMB), from propene that has been obtained by a method described above. Afterwards, propene undergoes a controlled oxidation by atmospheric oxygen in a gas phase in the presence of catalysts based on molybdenum and/or bismuth oxides, in order to form acrolein.

After purification, acrolein that has been obtained directly according to the invention or after purification is reacted with methylmercaptan (MSH) in order to produce the aldehyde-3-(methylthio)propionic acid (or MMP). In a subsequent step, the MMP is brought into contact with hydrocyanic acid in order to produce the 2-hydroxy-4-methylthiobutyronitrile acid (HMTBN). After the synthesis of HMTBN, various reaction steps result in methionine, its analogous hydroxy derivative (HMTBA), the esters of the latter, or its analogous oxo derivative (KMB). All these steps, starting from the synthesis of propene, are well known by those skilled in the art.

Another object of the present invention consists in producing acrylic acid, acrylonitrile and polypropylene from propene according to methods that are well known by those skilled in the art, which propene has been obtained by any of the above-described methods.

Hereinafter, the invention is illustrated through the following examples which show its details and its advantages in comparison with the prior art, and with reference to the figures according to which:

The illustrated catalysts are characterized by the following parameters:
- The specific surface, expressed in $m^2/g$ and measured by the BET method,
- the phosphor content and the metal(s) M content, expressed by a molar ratio P/M, and measured by ICP-OES (Inductively Coupled Plasma-Optical Emission Spectroscopy); in the following examples, this ratio varies within the preferred range that has been previously defined, from 0.9 to 1.5; more specifically, for the catalysts of the invention that are tested hereinafter, the molar ratio P/La is 1.10 for $LaPO_4$, and the molar ratio P/Nd is 1.14 for $NdPO_4$.

The dehydration reaction of the alcohols has been carried out on the indicated catalysts, at atmospheric pressure or at a substantially higher pressure, in a fixed bed reactor. The reactor is placed in a furnace which allows keeping the catalyst at the temperature of reaction which varies between 130 and 390° C. The reactor is fed with alcohol by means of a saturator or a syringe pump in the presence of a flow of nitrogen. For each example, the relative molar ratio of alcohol to nitrogen is indicated. The weight hourly space velocity (WHSV) is expressed in grams of introduced alcohol by grams of catalyst and by hour.

EXAMPLE 1

A series of orthophosphates of rare earth metals (Nd, Sm, Gd) has been tested in the dehydration reaction of butan-1-ol for the conversion of butan-1-ol into but-2-ene, and compared with gamma-alumina.

The specific surface of each of the tested catalysts is 117 $m^2/g$ for $NdPO_4$, 82 $m^2/g$ for $SmPO_4$, 95 $m^2/g$ for $GdPO_4$ and 270 $m^2/g$ for $Al_2O_3$.

The reaction has been carried out at atmospheric pressure under the following conditions: WHSV=2.38 $h^{-1}$; butan-1-ol/$N_2$=1/82.6.

Figure 1:
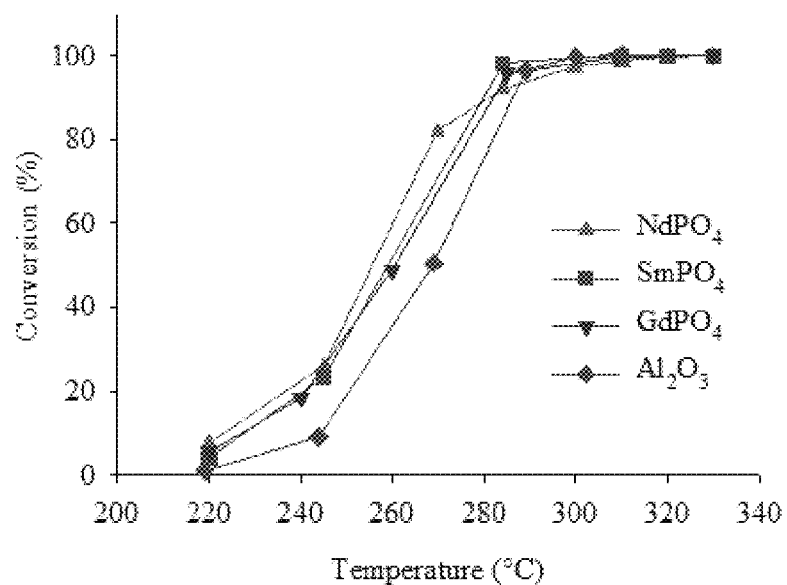
FIG. 1 represents a comparison of the variation of the conversion of butan-1-ol, according to the temperature of the reaction, for three catalysts of the invention and for an alumina, under the conditions that are described in Example 1.
Figure 2:
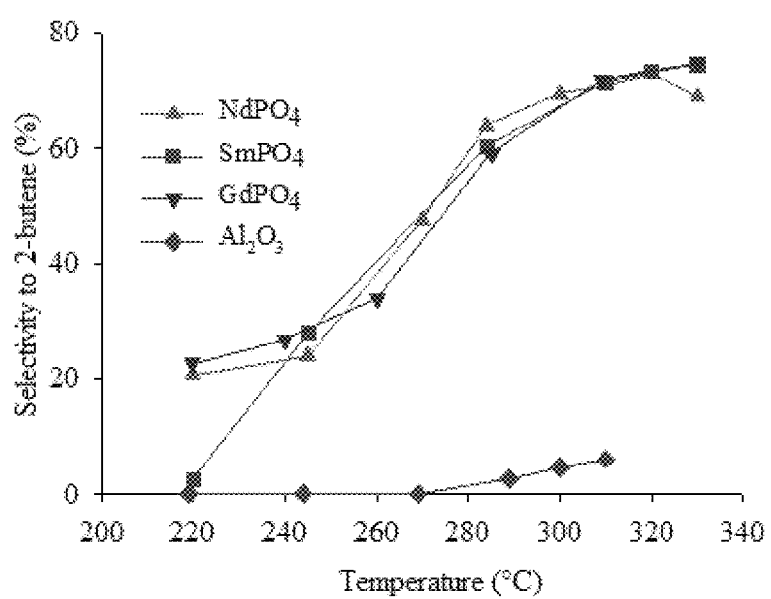
FIG. 2 represents a comparison of the selectivity to but-2-ene according to the temperature of the reaction for the three same catalysts of the invention and for the same alumina, as FIG. 1, under the conditions that are described in Example 1.

In FIGS. 1 and 2, there are shown respectively the conversion of butan-1-ol and the selectivity to but-2-ene according to the temperature of the reaction with the following legend:
▲ $NdPO_4$
■ $SmPO_4$
▼ $GdPO_4$
♦ $Al_2O_3$ It appears that the phosphates are active at a lower temperature than the reference alumina. Furthermore, a quite higher selectivity to but-2-ene has been measured.

EXAMPLE 2

In this example, the lanthanum orthophosphate is prepared form two different precursors, respectively, $Na_2HPO_4$ in accordance with the production method described in J. A. Diaz-Guillen, A. F. Fuentes, S. Gallini, M. T. Colomer, J. All. and Comp. 427 (2007) 87-98, and $(NH_4)H_2PO_4$ in accordance with the method of Pavel.

The specific surface of each of the tested catalysts is 128 $m^2/g$ for $LaPO_4$ that has been obtained from $Na_2HPO_4$, and 112 $m^2/g$ for $LaPO_4$ that has been obtained from $(NH_4)H_2PO_4$.

These catalysts have been tested in the dehydration of butan-1-ol under the following test conditions: WHSV=2.38 $h^{-1}$; butan-1-ol/$N_2$=1/82.6.

Figure 3:
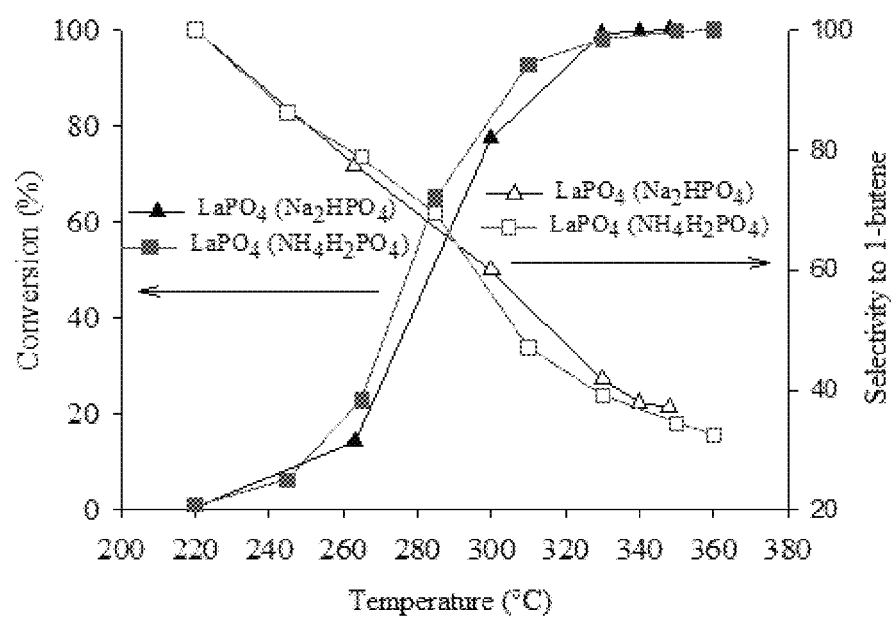
FIG. 3 represents a comparison of the conversion of butan-1-ol and the selectivity to but-2-ene, according to the temperature of the reaction, for a catalyst of the invention which has been prepared according to two different methods, under the conditions that are described in Example 2.

FIG. 3 shows the variation of the conversion of the alcohol and the selectivity to but-1-ene according to the temperature, with the following legend:
▲ (conversion) and △ (selectivity): $LaPO_4$ obtained from $Na_2HPO_4$
■ (conversion) and □ (selectivity): $LaPO_4$ obtained from $(NH_4)H_2PO_4$ It is observed that the catalytic properties of the catalysts of the invention do not depend on the used precursors.

EXAMPLE 3

In this example, the neodymium orthophosphate in two different polymorphic forms (rhabdophane and monazite), has been tested in the dehydration reaction of butan-1-ol.

The test conditions are as follows: WHSV=2.38 $h^{-1}$; butan-1-ol/$N_2$=1/82.6.

Table 1 shows the conversion of the alcohol and the selectivity to but-2-ene at 320° C.:

TABLE 1

| Catalyst | Conversion of butan-1-ol (%) | Selectivity to but-2-ene (%) | Selectivity to but-1-ene (%) |
|---|---|---|---|
| $NdPO_4$ rhabdophane | 99.8 | 73 | 27 |
| $NdPO_4$ monazite | 99.9 | 72 | 28 |

EXAMPLE 4

A 50/50 molar mixture of ethanol and butan-1-ol has been dehydrated on a catalyst $GdPO_4$ of the invention and on a gamma-alumina. The catalytic results, obtained at 360° C., are shown in Table 2 below.

The specific surface of the catalyst $GdPO_4$ of the invention is 95 $m^2/g$ and the specific surface of alumina is 270 $m^2/g$.

The test conditions are as follows: WHSV=2.34 $h^{-1}$; $N_2$=100 ml.

Both alcohols have been completely transformed on the phosphate catalyst. This transformation results in an ethylene/but-2-ene mixture which is characterized by a molar ratio of 1.4 and which may be used directly in a metathesis reaction in order to form propene. It is also observed that the phosphate catalyst is very stable.

TABLE 2

| Catalyst | Time (h) | Conversion of ethanol (%) | Conversion of butan-1-ol (%) | Selectivity to ethylene (%) | Selectivity to but-2-ene (%) |
|---|---|---|---|---|---|
| $GdPO_4$ | 1 | 100 | 100 | 100 | 74 |
| | 60 | 99 | 100 | 100 | 71 |
| $Al_2O_3$ | 1 | 100 | 100 | 99 | 16 |

EXAMPLE 5

The catalysts $LaPO_4$ and $NdPO_4$ have been compared with alumina in the dehydration of but-3-ene-1-ol.

The specific surface of the catalysts $NdPO_4$ and $LaPO_4$ of the invention are 117 m$^2$/g and 124 m$^2$/g, respectively, and the specific surface of alumina is 270 m$^2$/g.

The reaction conditions are as follows: WHSV=2.49 h$^{-1}$; 3-but-1-ene-ol/$N_2$=1/76.8.

Table 3 below shows the conversion of the alcohol and the selectivity to butadiene at 286° C.

TABLE 3

| Catalyst | Conversion of 3-but-1-ene-ol (%) | Selectivity to butadiene (%) |
|---|---|---|
| $NdPO_4$ | 100 | 99 |
| $LaPO_4$ | 92 | 98 |
| $Al_2O_3$ | 34 | 12 |

EXAMPLE 6

$NdPO_4$ has been tested and compared with alumina in the dehydration of isobutanol.

The specific surface of the catalyst $NdPO_4$ of the invention is 117 m$^2$/g and the specific surface of alumina is 270 m$^2$/g.

The reaction conditions are as follows: WHSV=2.38 h$^{-1}$; isobutanol/$N_2$=1/82.6.

The conversion of isobutanol and the selectivity to isobutene and to but-2-ene at 245° C., are given in the following Table 4.

TABLE 4

| Catalyst | Conversion of isobutanol (%) | Selectivity to isobutene (%) | Selectivity to but-2-ene (%) |
|---|---|---|---|
| $NdPO_4$ | 52 | 91 | 9 |
| $Al_2O_3$ | 20 | 98 | 2 |

EXAMPLE 7

$NdPO_4$ has been tested in the dehydration reaction of butan-2-ol and compared with alumina.

The specific surface of the catalyst $NdPO_4$ of the invention is 117 m$^2$/g and the specific surface of alumina is 270 m$^2$/g.

The reaction has been carried out at atmospheric pressure under the following conditions: WHSV=2.38 h$^{-1}$; butan-2-ol/$N_2$=1/82.6; temperature of the reactor=200° C.

TABLE 5

| Catalyst | Conversion of butane-2-ol (%) | Selectivity to but-2-ene (%) |
|---|---|---|
| $NdPO_4$ | 76 | 84 |
| $Al_2O_3$ | 52 | 81 |

EXAMPLE 8

In this example, the neodymium phosphate has been tested in the dehydration of propan-1-ol.

The specific surface of the catalyst $NdPO_4$ of the invention is 117 m$^2$/g.

The reaction has been carried out at atmospheric pressure under the following conditions: WHSV=3.04 h$^{-1}$; propan-1-ol/$N_2$=1/49.5; temperature of the reactor=330° C.

The conversion of propan-1-ol and the selectivity to propene are shown in the following Table 6.

TABLE 6

| Catalyst | Conversion of propan-1-ol (%) | Selectivity to propene (%) |
|---|---|---|
| $NdPO_4$ | 99 | 99 |

EXAMPLE 9

The neodymium phosphate has been tested as a catalyst in the dehydration of butane-2,3-diol.

The specific surface of the catalyst $NdPO_4$ of the invention is 117 m$^2$/g.

The reaction has been carried out under the following conditions:

WHSV=2.95 h$^{-1}$; butane-2,3-ol/$N_2$=1/80.3; temperature of the reactor=320° C.

The catalytic results that have been obtained are shown in the following Table 7.

TABLE 7

| Catalyst | Conversion of butane-2,3-diol (%) | Selectivity to butadiene (%) |
|---|---|---|
| $NdPO_4$ | 99 | 60 |

The catalyst is very active and selective to butadiene.

EXAMPLE 10

The phosphates of Lanthanum, Neodymium and Gadolinium have been tested as catalysts in the dehydration of butane-2,3-ol (2,3-BDO).

The reaction conditions are as follows: WHSV=2.98 h$^{-1}$; $m_{cata}$=101 mg; contact time (W/F)=30.28 $g_{cata}$·h·mol$_{2,3\text{-}BDO}^{-1}$; $N_2$=100 ml·min$^{-1}$ and a gaseous mixture butane-2,3-ol/$N_2$=1/80.3.

The catalytic results that have been obtained are shown in the following Table 8.

TABLE 8

| Catalyst | Temperature (° C.) | Conversion of 2,3-BDO (%) | Selectivity to butadiene (%) | Selectivity to MEK (%) | Selectivity to MPA (%) |
|---|---|---|---|---|---|
| $LaPO_4$ | 300 | 95.4 | 56 | 7 | 37 |
| $NdPO_4$ | 320 | 100 | 58 | 7 | 35 |
| $GdPO_4$ | 300 | 100 | 60 | 7 | 33 |

The catalysts are very active and selective to butadiene.

EXAMPLE 11

The catalyst $GdPO_4$ has been tested in the dehydration of 3-butene-2-ol.

The reaction conditions are as follows: $m_{cata}$=101 mg; contact time (W/F)=28.97 $g_{cata}$·h·mol$^{-1}$; 3-butene-2-ol/$N_2$=1/76.8.

Table 9 shows the conversion of 3-butene-2-ol and the selectivity to butadiene at 230° C.

TABLE 9

| Catalyst | Conversion of 3-butene-2-ol (%) | Selectivity to butadiene (%) |
|---|---|---|
| GdPO$_4$ | 100 | 99 |

The catalyst is very active and selective to butadiene.

EXAMPLE 12

The catalyst GdPO$_4$ has been tested as a catalyst for the dehydration of but-3-ene-1,2-diol.

The reaction conditions are as follows: $m_{cata}$=118 mg; contact time (W/F)=30.3 $g_{cata}$·h·mol$^{-1}$; Alcohol/N$_2$=1/68; T=310° C.

The catalytic results that have been obtained are shown in the following Table 10.

TABLE 10

| Catalyst | Conversion of 3-butene-1,2-ol (%) | Selectivity to butenal (%) | Selectivity to butadiene (%) | Selectivity to other products* (%) |
|---|---|---|---|---|
| GdPO$_4$ | 96 | 98 | 1 | 1 |

*Other products: methyl vinyl ketone, 1,3-butadienol, 2,5-dihydrofurane

EXAMPLE 13

SmPO$_4$ has been tested in the reaction of the joint dehydration of ethanol, propanol and butanol.

The reaction has been carried out at atmospheric pressure under the following conditions:

contact time (W/F)=28.33 $g_{cata}$·h·mol$^{-1}$;
Ethanol/1-propanol/2-propanol/2-butanol=10/15/15/60;
N$_2$=100 ml·min$^{-1}$;
temperature of the reactor=330° C.

As indicated in the following Table 11, it is observed, at this temperature, a 100% conversion of all alcohols and practically a 100% selectivity to the corresponding alkenes.

TABLE 11

| Catalyst | Conversion of ethanol (%) | Selectivity to ethylene (%) | Conversion of 1- et 2- propanol (%) | Selectivity to propene (%) | Conversion of 2- butanol (%) | Selectivity to 1-/2- butene (%) |
|---|---|---|---|---|---|---|
| NdPO$_4$ | 99.1 | 100 | 100 | 99.5 | 100 | 27/73 |
| SmPO$_4$ | 100 | 100 | 100 | 100 | 100 | 24/76 |

EXAMPLE 14

The catalysts SmPO$_4$ and NdPO$_4$ have been studied in the dehydration of an ABE mixture (acetone/butanol/ethanol) which has been obtained by fermentation.

The test has been carried out at atmospheric pressure under the following conditions:

$m_{cata}$=101 mg;
contact time (W/F)=28.1 $g_{cata}$·h·mol$^{-1}$;
Acetone/1-butanol/ethanol=3/6/1;
N$_2$=100 ml·min$^{-1}$;
temperature of the reactor=330° C.

The following Table 12 shows the results.

TABLE 12

| Catalyst | Conversion of acetone (%) | Conversion of ethanol (%) | Selectivity to ethylene (%) | Conversion of 1-butanol (%) | Selectivity to 1-/2-butene (%) |
|---|---|---|---|---|---|
| NdPO$_4$ | 0 | 100 | 100 | 100 | 34/66 |
| SmPO$_4$ | 0 | 100 | 100 | 100 | 30/70 |

EXAMPLE 15

When produced by fermentation, the butane-2,3-ol (2,3-BDO) is mixed with a significant quantity of water which has to be eliminated by evaporation. If this separation could be completely or partially avoided prior to the step of dehydration into butadiene, this would surely be interesting from an economic point of view.

The Gadolinium phosphate has been tested in the presence of water.

Figure 4:
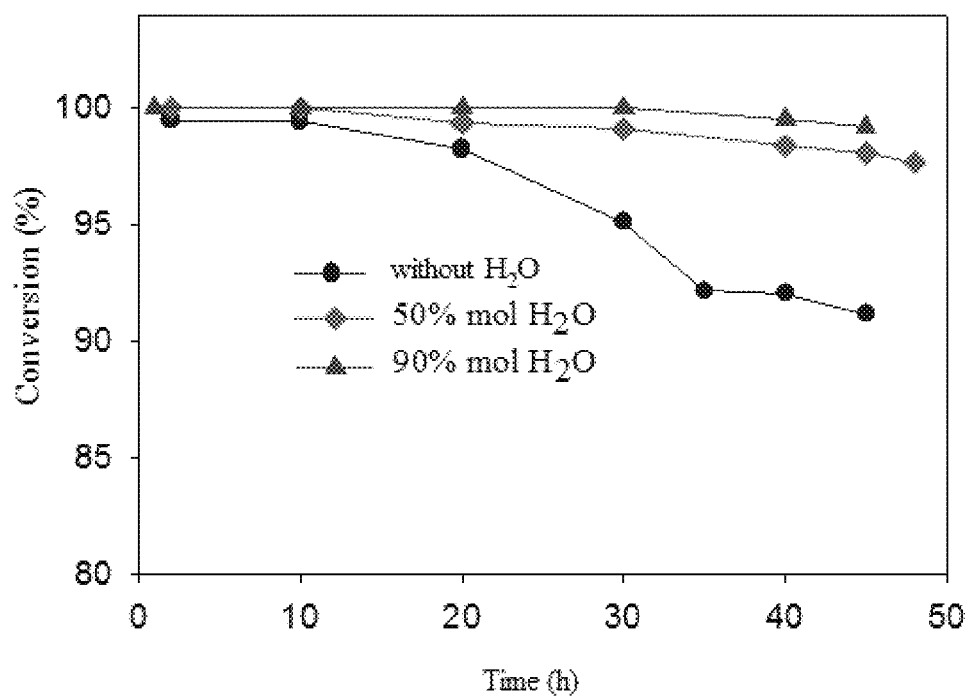
FIG. 4 shows the effect of water on the dehydration of butane-2,3-ol into butadiene, under the conditions that are described in Example 15.

The reaction has been carried out under the following conditions:

Temperature=300° C.; $m_{cata}$=101 mg; contact time (W/F)= 30.28 $g_{cata}$·h·mol$_{2,3-BDO}^{-1}$; N$_2$=100 ml·min$^{-1}$ The results are shown in the following Table 13 and illustrated in FIG. 4.

TABLE 13

| Catalyst | Water (% mol) | Conversion of butane-2,3-ol (%) | Selectivity to butadiene (%) | Selectivity to MEK (%) | Selectivity to MPA (%) |
|---|---|---|---|---|---|
| GdPO$_4$ | 0 | 100 | 60 | 7 | 33 |
|  | 50 | 100 | 50 | 10 | 40 |
|  | 90 | 100 | 43 | 13 | 44 |

It is observed that an increase of the quantity of water does not significantly modify the catalytic properties but slightly lowers the selectivity to butadiene.

The effect of water on the stability of the catalyst under the reaction conditions has also been studied. Water has a quite positive effect on this stabilization.

EXAMPLE 16

A 50/50 molar mixture of ethanol and 1-butanol has been dehydrated on phosphates of Gadolinium, Samarium and Neodymium.

The catalytic reaction conditions are as follows:

$m_{cata}$=101 mg; contact time (W/F)=25 $g_{cata}$·h·mol$^{-1}$;
N$_2$=100 ml·min$^{-1}$ The catalytic results that have been obtained are shown in Table 14 below.

TABLE 14

| Catalyst | Temperature (° C.) | Conversion of ethanol (%) | Conversion of 1-butanol (%) | Selectivity to ethylene (%) | Selectivity to 2-butene (%) |
|---|---|---|---|---|---|
| GdPO$_4$ | 360 | 100 | 100 | 100 | 74 |
| SmPO$_4$ | 360 | 99.8 | 100 | 100 | 75 |
| NdPO$_4$ | 350 | 97.8 | 100 | 100 | 73 |

Both alcohols have been completely transformed on the catalysts. For both dehydration reactions, the catalysts are very active and selective. The catalyst SmPO$_4$ is more selective to 2-butene.

The invention claimed is:

1. A method for preparing an olefine, a diene or a polyene, by catalytic conversion of at least one alcohol having a carbon chain of at least three carbon atoms different from propan-2-ol, in the presence of at least one catalyst of at least one phosphate of a metal M, M being chosen from Lanthanum, Praseodymium, Neodymium, Promethium, Samarium, Europium, Gadolinium, Terbium, Dysprosium, Holmium, Erbium, Thulium, Ytterbium, Lutetium, Yttrium, and Scandium, wherein said olefine, diene or polyene is obtained by catalytic conversion of said alcohol or mixture of corresponding alcohols, having a carbon chain of the same number of carbon atoms.

2. The method according to claim 1, wherein the metal(s) are chosen from among Lanthanum, Neodymium, Gadolinium and Samarium.

3. The method according to claim 1, wherein said catalyst is doped by at least one alkali metal chosen from among Cesium, Rubidium and Potassium and/or a transition metal chosen from among groups 4 to 7.

4. The method according to claim 1, wherein the molar ratio P/M varies from 0.5 to 2, M representing the metal or the sum of the metals M which constitute said catalyst.

5. The method according to claim 4, wherein the molar ratio P/M varies from 0.9 to 1.5.

6. The method according to claim 1, wherein the catalyst is regenerated by air or by diluted air which has been enriched in situ or ex situ.

7. The method according to claim 1, wherein the catalyst comprises an active phase and a support and/or a binder and/or the catalyst is formed.

8. The method according to claim 7, wherein the support and/or the binder are constituted by pure silica ($SiO_2$), a silica of an alkali metal, of an alkaline earth metal or of rare earth metals, titanium oxide ($TiO_2$), boron oxide ($B_2O_3$) or resins (sulphonic resins, perfluorosulfonicresins) and their mixtures.

9. The method according to claim 1, wherein the conversion is carried out in a gas phase.

10. The method according to claim 9, wherein the conversion is carried out in a fixed bed reactor, a fluidized bed reactor or a circulating fluidized bed reactor with backup with an oxidant (O2, CO2, H2O, etc.) or a zone-type reactor TZFBR (two zone fluidized bed reactor).

11. The method according to claim 1, wherein the conversion is carried out in a liquid phase.

12. The method according to claim 1, wherein the alcohol or the alcohols are pure, partially purified, unpurified, or in the form of azeotropic compositions, and mixtures of these.

13. The method according to claim 1, wherein the alcohol or the alcohols are in an aqueous solution, at a concentration of at least 1% weight.

14. The method according to claim 1, wherein the alcohol or the alcohols are chosen from among propan-1-ol, butan-1-ol, butan-2-ol, isobutanol, but-3-ene-1-ol, but-2-ene-1-ol, but-3-ene-1,2-diol, butane-2,3-diol, butane-1,3-diol, butane-1,4-diol, propane-1,2-diol, propane-1,3-diol, erythritol, and their mixtures.

15. A method for selective preparation of but-2-ene from butan-1-ol, butan-2-ol, and their mixtures, according to claim 1.

16. A method for preparing isobutene from isobutanol, according to claim 1.

17. A method for preparing a mixture of olefines, dienes and/or polyenes, according to claim 1.

18. A method for preparing a mixture of at least two olefines, dienes and/or polyenes, characterized in that one of the olefines, dienes and/or polyenes is prepared by a method according to claim 1.

19. The method according to claim 18, wherein the at least other olefine(s), diene(s) and/or polyene(s) are obtained by catalytic conversion of an alcohol or a mixture of alcohols, in the presence of at least one catalyst based of at least one phosphate of at least one metal M, said metal M being chosen from among the 15 lanthanides (Lanthanum, Cerium, Praseodymium, Neodymium, Promethium, Samarium, Europium, Gadolinium, Terbium, Dysprosium, Holmium, Erbium, Thulium, Ytterbium, Lutetium), Yttrium, Scandium and Boron.

20. The method according to claim 19, wherein the catalysts are identical or different.

21. The method according to claim 19, wherein said catalyst used for the preparation of the other olefine(s), diene(s), polyene(s) comprises an active phase and a support and/or a binder and/or the catalyst is formed, possibly in the presence of a binder.

22. The method according to claim 18, wherein said catalyst used for the preparation of the other olefine(s), diene(s), polyene(s) is regenerated.

23. The method according to claim 17, wherein the at least two olefines, dienes, polyenes are prepared in the same reactor or in different reactors.

24. A method for producing butadiene, characterized in that it implements a method according to claim 1, wherein the alcohol is chosen from among but-2-ene-1-ol, but-3-ene-1-ol, but-1-ene-3-ol, but-3-ene-1,2-diol, butane-2,4-diol, butane-1,3-diol, butane-2,3-diol, and butane-1,4-diol and their mixtures.

* * * * *